(12) United States Patent
Denner et al.

(10) Patent No.: US 9,535,184 B2
(45) Date of Patent: Jan. 3, 2017

(54) SENSOR MODULE AND ELECTRODE FOR A SENSOR MODULE

(71) Applicants: Schunk Wien Gesellschaft mbH, Vienna (AT); Texplor Austria GmbH, Vienna (AT)

(72) Inventors: Gerhard Denner, Vienna (AT); Werner Plach, Eichgraben (AT)

(73) Assignee: SCHUNK WIEN GESELLSCHAFT M.B.H., Vienna (AT)

( * ) Notice: Subject to any disclaimer, the term of this patent is extended or adjusted under 35 U.S.C. 154(b) by 207 days.

(21) Appl. No.: 14/349,268

(22) PCT Filed: Oct. 2, 2012

(86) PCT No.: PCT/EP2012/069493
§ 371 (c)(1),
(2) Date: Apr. 2, 2014

(87) PCT Pub. No.: WO2013/050387
PCT Pub. Date: Apr. 11, 2013

(65) Prior Publication Data
US 2014/0320135 A1    Oct. 30, 2014

(30) Foreign Application Priority Data

Oct. 4, 2011    (DE) .................. 10 2011 083 989

(51) Int. Cl.
*G01V 3/00*    (2006.01)
*G01N 33/24*    (2006.01)
(Continued)

(52) U.S. Cl.
CPC ................. *G01V 3/00* (2013.01); *G01N 33/24* (2013.01); *B01J 2/00* (2013.01); *B01J 20/00* (2013.01); *C01B 2201/00* (2013.01)

(58) Field of Classification Search
CPC .............. B01J 2/00; B01J 20/00; B01J 39/00; B01J 2203/00; C01B 2201/00
See application file for complete search history.

(56) References Cited

U.S. PATENT DOCUMENTS 4,282,080 A * 8/1981 Muller ............... G01N 27/4067
204/412
4,334,974 A * 6/1982 Muller ............... G01N 27/4071
204/425

(Continued)

FOREIGN PATENT DOCUMENTS

CN    201829626 U    5/2011
CN    201868585 U    6/2011

(Continued)

OTHER PUBLICATIONS

International Search Report as mailed on Dec. 19, 2012 for International Application No. PCT/EP2012/069493.

(Continued)

*Primary Examiner* — Jermele M Hollington
*Assistant Examiner* — Temilade Rhodes-Vivour
(74) *Attorney, Agent, or Firm* — Quarles & Brady LLP

(57) ABSTRACT

The invention relates to a sensor module (10) for measuring an electrical variable, comprising at least one electrode (12, 13), which is arranged in a housing (58) made of an electrically insulating material and which can be connected to an electrical measuring device by means of a connecting cable, wherein the electrode has a sensor element, which is arranged between an inner and an outer contact plate (26,27) made of a carbon material and which is coupled to the connecting cable, wherein an outer contact plate (27) of the electrode is arranged in an outer face of the housing.

22 Claims, 2 Drawing Sheets

(51) Int. Cl.
 *B01J 2/00* (2006.01)
 *B01J 20/00* (2006.01)

(56) References Cited

U.S. PATENT DOCUMENTS

| | | | | |
|---|---|---|---|---|
| 5,001,531 | A * | 3/1991 | Yamaguchi | G01N 27/414 204/294 |
| 5,221,456 | A * | 6/1993 | Benton | G01N 27/333 204/416 |
| 8,309,024 | B2 * | 11/2012 | Redko | G01N 27/221 422/401 |
| 2009/0321257 | A1 * | 12/2009 | Takahara | G01N 27/3272 204/403.14 |

FOREIGN PATENT DOCUMENTS

| | | |
|---|---|---|
| DE | 28 22 769 | 12/1978 |
| DE | 102004023712 A1 | 12/2005 |
| EP | 0 354 733 | 2/1990 |
| GB | 1 586 751 | 3/1981 |
| JP | 2011013025 A | 1/2011 |
| WO | 0016424 A1 | 3/2000 |
| WO | 2009/157755 | 12/2009 |

OTHER PUBLICATIONS

State Intellectual Property Office of People's Republic of China, First Office Action and Search Report, Application No. 201280059680.3, Mar. 23, 2015, 10 pages [English Language Translation Only].

State Intellectual Property Office of People's Republic of China, Second Office Action and Search Report, Application No. 201280059680.3, Jan. 11, 2016, 11 pages [English Language Translation Only].

* cited by examiner

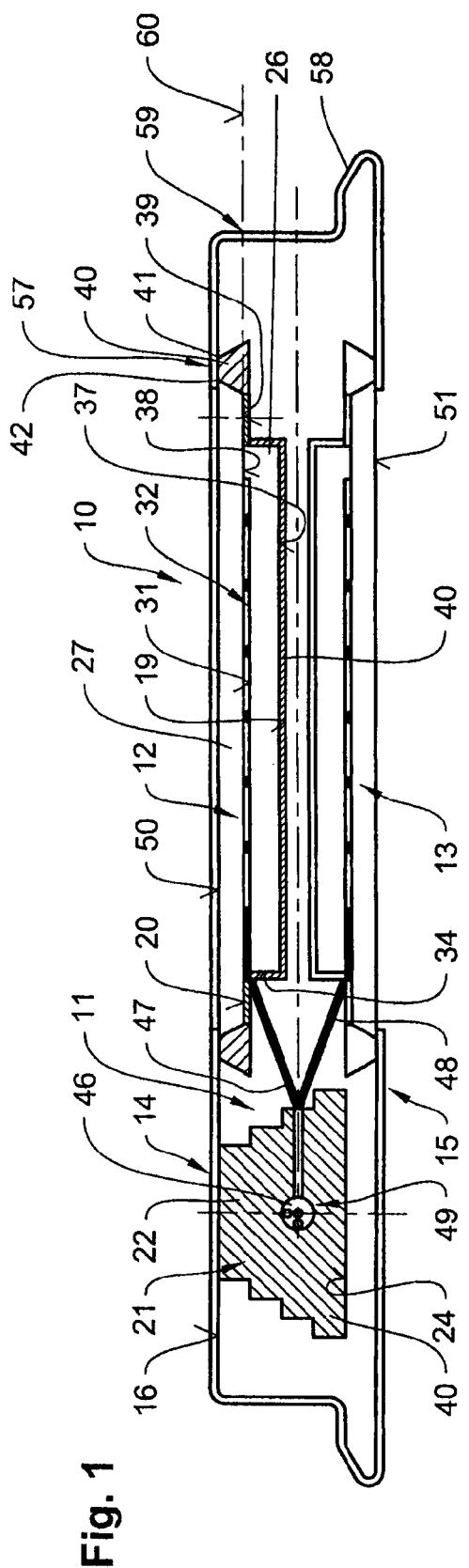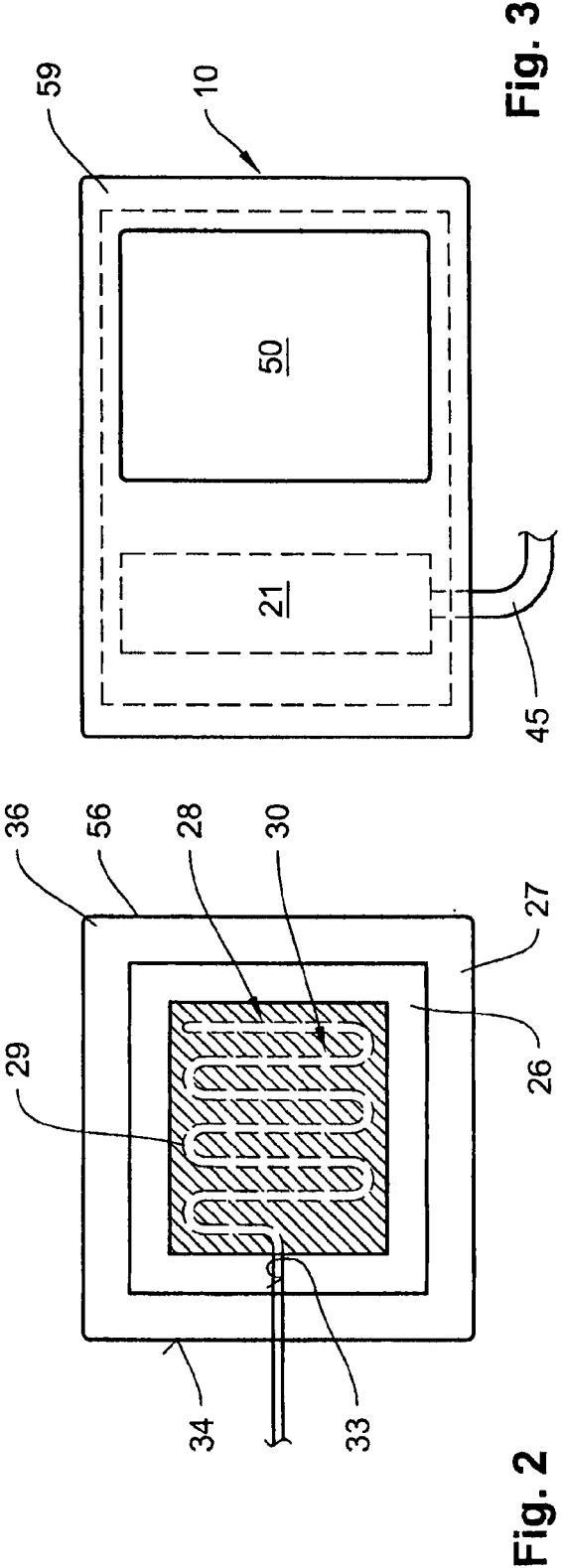

SENSOR MODULE AND ELECTRODE FOR A SENSOR MODULE

CROSS-REFERENCE TO RELATED APPLICATIONS

This application represents the national stage entry of PCT International Application No. PCT/EP2012/069493 filed Oct. 2, 2012 and claims the benefit of German Patent Application No. 10 2011 083 989.5 filed Oct. 4, 2011. The contents of both of these applications are hereby incorporated by reference as if set forth in their entirety herein.

The invention relates to a sensor module for measuring an electrical variable, comprising at least one electrode, which is arranged in a housing made of an electrically insulating material and which can be connected to an electrical measuring device by means of a connecting cable, as well as to a corresponding electrode.

Sensor modules of the type mentioned at the beginning can be used for determining local electrical variables, such as the resistance, the amperage or the voltage, in a solid state environment, for instance in the ground. Since electrical variables, such as the electrical resistance, change in the ground, as it is well known, as a function of the composition of the ground, in particular as a function of the ground formation and of the liquid content or of the liquid distribution in the ground, such sensor modules are, for instance, used to detect leakages in seals of waste disposal sites and storage points. Depending on the type of the disposal storage material, the sensor modules are exposed to a partially considerable aggressive environment here, such that it is essential for the functional reliability of the sensor modules, in addition to the good electrical conductivity of the contact surfaces of the sensor modules, that said modules turn out to be chemically stable. Moreover, it is, as a matter of course, very essential for the functional reliability of sensor modules of the type mentioned at the beginning that they have sufficient mechanical stability to withstand the mechanical loads occurring in the ground.

Therefore, the present invention is based on the task of proposing a sensor module, which, in addition to a good electrical conductivity, which means a small contact resistance, has a large chemical stability and, moreover, a large mechanical stability. These requirements, as a matter of course, particularly relate to the electrodes, which are arranged in the sensor module and which have direct contact to the environment, thus correspondingly directly being exposed to the environmental influences.

For solving this object, the sensor module in accordance with the invention has the features of claim 1. The electrode in accordance with the invention has the features of claim 16.

In accordance with the invention, the electrode of the sensor module has a sensor element, which is arranged between an inner and an outer contact plate made of a carbon material and which is coupled to the connecting cable, wherein an outer contact plate of the electrode is arranged in an outer face of the housing. By arranging the sensor element, which can for instance consist of a sensor wire, which is embodied to be meander-shaped, between the two contact plates made of a carbon material, housing the sensor element is enabled, which, in addition to a good electrical conductivity, offers a mechanical protection of the sensitive sensor element, and, moreover, has the chemical stability which is also necessary for the functional reliability of the sensor element in a chemically aggressive environment.

Preferably, the sensor element can be formed of a non-corrosive material or of a material, which is provided with a noncorrosive coating. For instance, the sensor element can have a gold coating.

As a whole, by means of the sandwich-like reception of the sensor element between the contact plates made of carbon, a protective shielding of the sensor element against mechanical and chemical loads as well as, simultaneously, a secure electrical contacting between the surrounding area, which faces the contact plates and which is, for instance, formed by the ground, and the sensor element, which is arranged between the contact plates.

An electrically conductive plate, which is produced as a gas-tight and liquid-tight plate in a hot pressing process from a carbon material that has a mixture of a thermosetting material and carbon particles, and which, after the molding operation, has been carbonized and impregnated for achieving the gas-tightness and liquid tightness, is particularly suitable for being used as the contact plate. Producing such a plate which is characterized by a high structural stability is described in the document WO 2000/016424, the disclosure thereof being incorporated hereby.

Advantageously, the sensor element can already be arranged in the carbon material of such a contact plate during the molding operation of the contact plate, such that, in the finished contact plate, the sensor element is received so as to be embedded in the contact plate.

In order to enable a defined arrangement of the sensor element between the contact plates, it is advantageous if, for arranging the sensor element between the contact plates, a receiving chamber, which is embodied in a coupling plane of the contact plates, is embodied.

In order to enable the most secure contacting possible between the sensor element and the contact plates, the receiving chamber, for embedding the sensor element, can be filled with an electrically conductive filling compound, wherein carbon, for instance in an embodiment as a so-called "ramming compound", is particularly suitable here, which compound is filled into the receiving chamber after arranging the sensor element in the receiving chamber and can be compressed in the same, such that a particularly low contact resistance between the sensor element and the contact plates made of carbon can be realized.

It is also particularly advantageous if the receiving chamber is embodied in at least one contact plate surface by a recess, which is adapted to the structure of the sensor element, wherein the receiving chamber is preferably embodied by a milled indentation in the contact plate surface.

A particularly secure and protected arrangement of the electrode becomes possible if the electrode is arranged on a side of a support plate of the housing, in such a manner that the contact plates of the electrode are arranged in an electrode reception in a support plate surface.

If the electrode reception is provided with a bearing edge, which is embodied at a receiving bottom of the electrode reception, in such a manner that the inner contact plate is arranged on the receiving bottom and the outer contact plate is arranged on the bearing edge, a particularly secure bond between the electrode and the housing or the support plate is possible.

For fixing the electrode or the contact plates at the support plate as well as, simultaneously, for sealing the electrode against the environment, it is advantageous if an edge gap, which is formed between the outer contact plate and an opening edge of the electrode reception in the support plate surface, is filled with a nonconductive curing plastic material.

In order to further strengthen an adhesive bonding between the electrode and the support plate, the bottom of the electrode reception as well as, if required, additionally also the bearing edge can also be provided with a coating made of a nonconductive curing plastic material, such that the largest possible surface of the electrode is adhesively coupled to the support plate.

In particular for carrying out the measurement of an electrical difference in potential with the aid of only one sensor module, it is advantageous if the sensor module has two electrodes in the housing, which electrodes are electrically insulated with respect to each other, and which can be connected to an electrical measuring device by means of a connecting cable, wherein the sensor elements of the electrodes are respectively coupled to the connecting cable, and wherein one outer contact plate respectively of each electrode is arranged in an outer face of the housing. In this way, instead of using two separate sensor modules, only one sensor module, which is provided with two electrodes, is used.

In a particularly advantageous relative arrangement of the two electrodes, the electrodes are situated on two opposite sides of the support plate of the housing, in such a manner that the contact plates of an electrode are respectively arranged in an electrode reception in a support plate surface. Thus, for instance when integrating the support plate into an extensively sealing medium or sealing element, said sealing element can be permanently monitored.

It is particularly advantageous for a reception of the electrodes into the housing of the sensor module, which reception is sealed against external influences if the support plate, next to the electrode receptions, which are arranged so as to be opposite from each other, in the support plate surface has a cable reception for receiving a cable coupling, which is provided between a connecting end of the connecting cable and sensor wire ends of the sensor elements, wherein, for providing the coupling of the connecting cable to the sensor wire ends, the electrode receptions are coupled to the cable reception by means of cable channels.

For fixing the connecting cable in the cable reception or at the housing of the sensor module, it turns out to be advantageous if the cable reception is filled with a nonconductive curing plastic material.

In particular in the event that a material that deviates from the material of the support plate is used for filling the cable reception as well as, if required, for filling the edge gap, which is formed between the outer contact plates of the electrodes and the support plate, which means, for instance in the event that a polyethylene, in particular a high-density polyethylene (HDPE) is used for the support plate, and a polyurethane (PU) material is used for the filling material, it is advantageous if the support plate, at least on the surface that has the cable reception, is provided with a coating, for instance provided with a plastic foil, which, in the event that a polyethylene is selected as the material for the support plate, is advantageously embodies as a polyethylene foil. Thus, the support plate can for instance be shrink-wrapped into foil systems as a permanent monitoring sensor system.

Also independently from the use for embodying a sensor module of the type mentioned at the beginning, an electrode which is embodied in accordance with the invention, and which has a sensor element between an inner and an outer contact plate made of a carbon material, has the essential advantages described at the beginning, namely that such electrodes turn out to be particularly reliable in operation even in a chemically aggressive environment due to the shielding of the sensor element with the aid of the contact plates and due to the advantageous electrical properties of the contact plates.

Both the sensor module in accordance with the invention and the electrode in accordance with the invention are suitable—in particular due to the carbon material used—for use in medical engineering. Here, in particular in a correspondingly embodied sensor module, comprising an electrode or electrodes, which is or are received in the electrode reception of the support plate so as to be sealed with respect to the outside, the use in body fluids is possible.

An advantageous embodiment of the sensor module in accordance with the invention as well as preferred design of an electrode in accordance with the invention, which is utilized in the sensor module, will be described in greater detail hereinafter using the drawings.

In the figures:

FIG. 1 shows a cross-sectional illustration of a sensor module comprising two electrodes, which are arranged in the surface of the sensor module comprising outer contact plates;

FIG. 2 shows a top view onto the sensor module, which is illustrated in FIG. 1;

FIG. 3 shows a top view onto an electrode of the sensor module, which is illustrated in FIG. 1;

Figure 4:
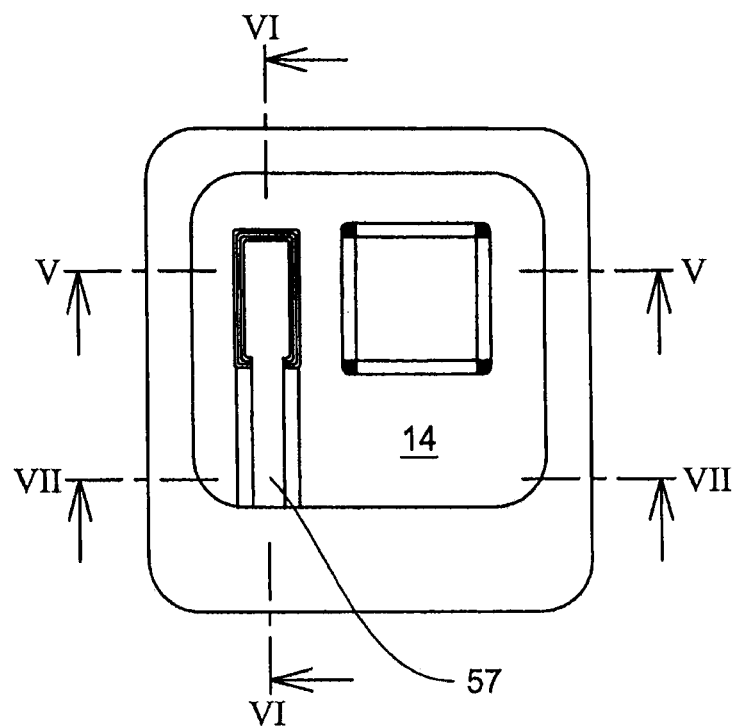
FIG. 4 shows a top view onto a support plate of the sensor module, which is illustrated in FIG. 1.

FIG. 1, in a cross-sectional illustration, shows an embodiment of a sensor module 10 comprising a support plate 11, which is manufactured from a high-density polyethylene (HDPE) in the exemplary embodiment that is illustrated here and has two electrodes 12, 13, which are inserted into the support plate 11.

The sensor module 10 is in particular suitable, by shrink-wrapping the support plates, for integration into foil sealing systems, and thus for embodying a permanent monitoring sensor system.

The support plate 11, which is illustrated in FIGS. 1 and 4 to 7, on two opposite sides 14, 15 has electrode receptions 17, 18, which are introduced into a support plate surface 16, and which are preferably generated by a milling processing of the support plate surface 16 and have a bearing edge 20, which is respectively embodied at a receiving bottom 19, which bearing edge is embodied so as to be frame-like in the present case. The bearing edge 20 is set back with respect to the support plate surface 16, such that, as a whole, the stepped cross-section of the electrode receptions 17, 18, which is illustrated in FIGS. 1, 4, 5 and 7, results.

Figure 5:
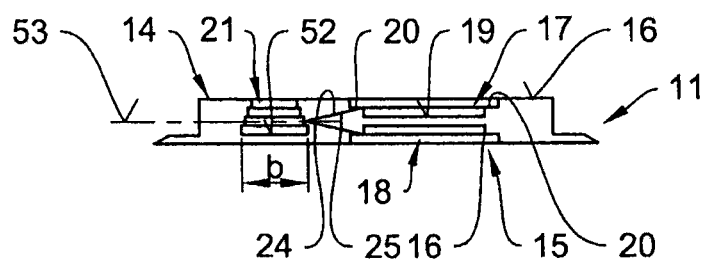
FIG. 5 shows a cross-sectional illustration of the support plate, which is illustrated in FIG. 4, in accordance with the cross-sectional line V-V in FIG. 4.
Figure 6:
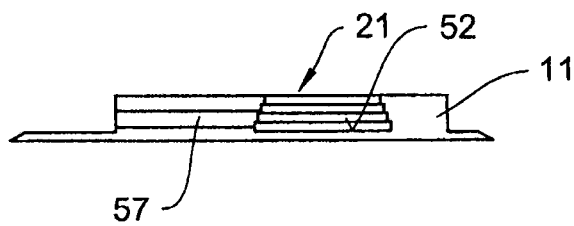
FIG. 6 shows a cross-sectional illustration of the support plate, which is illustrated in FIG. 4, in accordance with the cross-section line VI-VI in FIG. 4.
Figure 7:
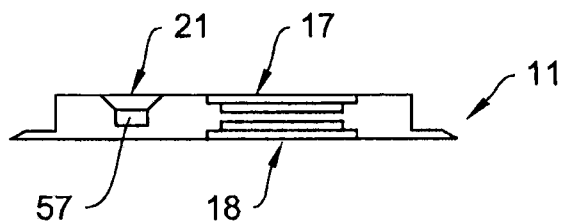
FIG. 7 shows a cross-sectional illustration of the support plate, which is illustrated in FIG. 4, in accordance with the cross-sectional line VII-VII in FIG. 4.

In addition to the two electrode receptions 17, 18, which are preferably introduced by milling here, the support plate 11 has a cable reception 21, which is in particular illustrated in FIGS. 1, 4 and 5, and which is preferably equally generated by milling and has a stepped cross-section 22 in the illustrated exemplary embodiment, the cross-section being composed of hollow spaces that are arranged above one another and so as to merge with one another and that are embodied so as to be cubic-shaped here, the width b thereof being reduced from a receiving bottom 52 towards the support plate surface 16, in such a manner that a receiving opening 23 is embodied in the support plate surface 16.

Furthermore, the support plate 11 has two cable channels 24, 25, which respectively couple the electrode receptions 17, 18 to the cable reception 21, and which extend into the cable reception 21 from an inner rim 16 of the bearing edge 20 of the electrode receptions 17, 18 so as to be inclined towards a coupling plane 53 (FIG. 5).

As it results from a combined view of FIGS. 1 and 3, the electrodes 12, 13 have one inner contact plate 26 and one outer contact plate 27 respectively, between which a sensor element 28 is arranged, which, in the present case, has a sensor wire 29 that is preferably coated with gold and that embodies a contact meander 30, the meander being arranged in a coupling plane 60 between the contact plates 26, 27 on a contact surface 31 of the inner contact plate 26 in a receiving chamber 32. In the contact surface 31 of the inner contact plate 26, a sensor wire channel 33 is equally situated, which channel couples the receiving chamber 32 to an outer edge 34 of the inner contact plate 26. In the relative arrangement of the inner contact plate 26 and of the outer contact plate 27 that protrudes above the inner contact plate 26 with an edge projection 56, which arrangement is illustrated in FIGS. 1 and 3, for the contact meander 30 of the sensor wire 29, a receiving space results, which is closed except for the sensor wire channel 33, and out of which a connecting end 55 of the sensor wire 29 is fed. For achieving a maximized contact surface between the contact meander 30 and the contact plates 26, 27, the receiving chamber 32 is filled with a carbon powder 35.

As it can be seen in particular from FIG. 1, the electrodes 12, 13 are arranged in the electrode receptions 17, 18 such that the outer contact plates 27 rest on the bearing edge 20 at least in contact plate corner areas 36 (FIG. 3). Preferably, in the exemplary embodiment, which is illustrated in FIG. 1, a mechanical bond between the inner contact plate 26 and the outer contact plate 27 is simultaneously produced with a mechanical bond between the electrodes 12, 13 and the support plate 11. Here, between a lower side 37 of the inner contact plate 26 and the receiving bottom 19 as well as between a bearing edge 39, which is embodied at a lower side 38 of the edge projection 56 of the outer contact plate 27, and the bearing edge 20 of the electrode receptions 17, 18, a glue made of a crosslinking plastic material 40, in particular a PU glue, is applied, which glue effects a stable mechanical bond between the electrodes 12, 13 and the support plate 11 after curing. Moreover, as is illustrated in FIG. 1, an edge gap 43, which is embodied between an opening edge 41 that is embodied in the support plate surface 16 and an outer edge 42 of the outer contact plates 27, is equally filled with the plastic material 40, such that a complete sealing between the electrodes 12, 13 and the support plate surface 16 has been generated at the support plate surface 16.

For increasing the stability of the mechanical bond between the support plate 11 and the electrodes 12, 13, which bond has been generated by means of the plastic material 40, in the exemplary embodiment, which is illustrated in FIG. 1, the edge gap 43 is provided with a gap cross-section 44, which is configured in the type of a dovetail and is tapered towards the support plate surface 16.

As it becomes apparent from a combined view of FIGS. 1 and 2, the support plate 11 is provided with a cable channel 57 (see also FIGS. 4 and 6), which leads into the cable reception 21 and serves for feeding through a connecting cable 45 of the sensor module 10, which is coupled to the sensor wire ends 47, 48 at its connecting end 46 (FIG. 1). For strain relief and, simultaneously, for a sealing reception of a cable coupling 49, which is configured between the sensor wire ends 47, 48 and the connecting end 46 of the connecting cable 45, the cable reception 21 is filled with the plastic material 40.

In order to embody a housing 58 that is continuously formed of a PE material, except for the contact faces 50, 51 of the outer contact plates 27 of the electrodes 12, 13, which faces remain freely accessible, the support plate 11, on its support plate surface 16, is covered or coated with a foil 59, such that the openings of the support plate 11, which are filled with the plastic material 40, which means the receiving opening 23 of the cable reception 21 and the edge gap 43, are covered by the foil.

The invention claimed is:

1. A sensor module for measuring an electrical variable, said sensor module comprising:
    a housing formed at least in part from an electrically insulating material, said housing including an outer face; and
    at least one electrode arranged in said housing and connectable to an electrical measuring device by a connecting cable, the electrode having a sensor element arranged between an inner and an outer contact plate made of a carbon material and said sensor is coupled to the connecting cable, wherein at least a portion of said outer contact plate of the electrode forms said outer face of said housing.

2. The sensor module according to claim 1, in which the sensor element is received so as to be embedded in the carbon material of a contact plate.

3. The sensor module according to claim 1, in which the contact plates, for arranging the electrode, have a receiving chamber in a coupling plane of the contact plates.

4. The sensor module according to claim 3, in which the receiving chamber, is filled with an electrically conductive filling compound embedding the sensor element.

5. The sensor module according to claim 4, in which the conductive filling compound is a powder containing carbon.

6. The sensor module according to claim 1, in which for measuring an electrical difference in potential or an electrical resistance, two electrodes are arranged in the housing so as to be electrically insulated with respect to each other, which electrodes can be connected to an electrical measuring device by means of the connecting cable, wherein the sensor elements of the electrodes are respectively coupled to the connecting cable, and wherein one outer contact plate respectively of each electrode is arranged in an outer face of the housing.

7. The sensor module according to claim 6, in which the electrodes are arranged on two opposite sides of the support plate of the housing, in such a manner that the contact plates of an electrode are respectively arranged in an electrode reception in a support plate surface.

8. The sensor module according to claim 7, in which the support plate, next to the electrode receptions, which are arranged so as to be opposite from each other, in the support plate surface has a cable reception for receiving a cable coupling, which is provided between a connecting end of the connecting cable and sensor wire ends of the sensor elements, wherein, for providing the coupling of the connecting cable to the sensor wire ends, the electrode receptions are coupled to the cable reception by means of cable channels.

9. The sensor module according to claim 8, in which the cable reception is filled with a nonconductive curing plastic material fixing the connecting cable in the cable reception 4.

10. The sensor module according to claim 8, in which the support plate, at least on the surface that has the cable reception, has a coating comprising a plastic foil.

11. An electrode, in particular for use with a sensor module according to claim 1, in which the electrode has a sensor element arranged between an inner and an outer contact plate made of a carbon material.

12. The electrode according to claim 11, in which the sensor element is embedded in the carbon material of a contact plate.

13. The electrode according to claim 11, in which the contact plates, for arranging the sensor element, have a receiving chamber in a coupling plane of the contact plates.

14. The electrode according to claim 13, in which the receiving chamber is filled with an electrically conductive filling compound embedding the sensor element.

15. The electrode according to claim 14, in which the conductive filling compound is a powder containing carbon.

16. The electrode according to claim 13, in which the receiving chamber is at least one contact surface of the contact plates by a recess adapted to the structure of the sensor element.

17. The electrode according to claim 16, in which the receiving chamber is embodied by a milled indentation in the contact surface of a contact plate.

18. A sensor module for measuring an electrical variable, said sensor module comprising:
  a housing made of an electrically insulating material;
  at least one electrode arranged in said housing and connectable to an electrical measuring device by a connecting cable, the electrode having a sensor element arranged between an inner and an outer contact plate made of a carbon material and said sensor is coupled to the connecting cable, wherein an outer contact plate of the electrode is arranged in an outer face of the housing, wherein the contact plates, for arranging the electrode, have a receiving chamber in a coupling plane of the contact plates, the receiving chamber is at least one contact surface of the contact plates by a recess adapted to the structure of the sensor element.

19. The sensor module according to claim 18, in which the receiving chamber is a milled indentation in the contact surface of a contact plate.

20. A sensor module for measuring an electrical variable, said sensor module comprising:
  a housing made of an electrically insulating material;
  at least one electrode arranged in said housing and connectable to an electrical measuring device by a connecting cable, the electrode having a sensor element arranged between an inner and an outer contact plate made of a carbon material and said sensor is coupled to the connecting cable, wherein an outer contact plate of the electrode is arranged in an outer face of the housing, wherein the at least one electrode is on a side of a support plate of the housing, in such a manner that the contact plates of the electrode are arranged in an electrode reception in a support plate surface.

21. The sensor module according to claim 20, in which the electrode reception is provided with a bearing edge at a receiving bottom, in such a manner that the inner contact plate is arranged on the receiving bottom and the outer contact plate is arranged on the bearing edge.

22. The sensor module according to claim 20, in which edge gaps, formed between the outer contact plate and an opening edge of the electrode reception in the support plate surface are filled with a nonconductive curing plastic material fixing the contact plates and sealing the electrode in the electrode reception of the support plate.

* * * * *